US009322071B2

United States Patent
Kwon et al.

(10) Patent No.: US 9,322,071 B2
(45) Date of Patent: Apr. 26, 2016

(54) METHOD FOR THE CONCENTRATION AND DETECTION OF VIRUS

(71) Applicants: Korea Basic Science Institute, Daejeon (KR); Industry Foundation of Chonnam National University, Gwangju (KR)

(72) Inventors: Joseph Kwon, Jeollabuk-Do (KR); Jong-Soon Choi, Daejeon (KR); Duwoon Kim, Gwangju (KR); Hee-Min Lee, Gwangju (KR)

(73) Assignees: Korea Basic Science Institute, Daejeon (KR); Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 14/499,801

(22) Filed: Sep. 29, 2014

(65) Prior Publication Data

US 2016/0090640 A1    Mar. 31, 2016

(51) Int. Cl.
  *C12Q 1/70* (2006.01)
  *C12N 7/00* (2006.01)

(52) U.S. Cl.
  CPC ........ *C12Q 1/701* (2013.01); *C12N 7/00* (2013.01); *C12Q 1/706* (2013.01); *C12N 2770/16021* (2013.01); *C12N 2770/32421* (2013.01)

(58) Field of Classification Search
  None
  See application file for complete search history.

(56) References Cited

U.S. PATENT DOCUMENTS 6,103,537 A * 8/2000 Ullman ............ G01N 27/44726
                                                                   204/451

FOREIGN PATENT DOCUMENTS

JP           2002165591 A       6/2002

OTHER PUBLICATIONS

Sanchez et al. Safety of the production process of SURFACEN(®) to inactivate and remove virus. Biologicals. Jul. 2013;41(4):254-60.*
Taube et al. Murine noroviruses bind glycolipid and glycoprotein attachment receptors in a strain-dependent manner. J Virol. May 2012;86(10):5584-93.*
Chen et al. Concanavalin A affinity chromatography for efficient baculovirus purification. Biotechnol Prog. Nov.-Dec. 2009;25(6):1669-77.*
Ayhan, F. Surface Modification and Covalent Coupling of Concanavalin A onto Poly(EGDMA/HEMA) Microbeads for Cell Affinity Applications. Journal of Bioactive and Compatible Polymers. 2003; 18(4):297-310.
Hong et al. A rapid, sensitive and selective electrochemical biosensor with concanavalin A for the preemptive detection of norovirus. Biosens Bioelectron. Feb. 15, 2015;64:338-44.

(Continued)

*Primary Examiner* — Michelle S Horning
(74) *Attorney, Agent, or Firm* — Mintz Levin Cohn Ferris Glovsky and Popeo, P.C.; Kongsik Kim; Linyu L. Mitra

(57) ABSTRACT

Disclosed is an economic method for concentrating virus and detecting virus, such that virus in a sample solution having low virus concentration can be concentrated with high efficiency within a short time. Particularly, the method comprising the steps of: (A) adding Concanavalin A (Con A) to a sample solution containing a virus, and reacting the added Concanavalin A with the virus in the sample solution to form a virus-Concanavalin A conjugate; and (B) separating the virus-Concanavalin A conjugate from the sample solution.

10 Claims, 15 Drawing Sheets

(56) References Cited

OTHER PUBLICATIONS

Khan et al. A Novel and Inexpensive Procedure for the Purification of Concanavalin a from Jack Bean (Canavalia ensiformis) Extract. European Journal of Applied Sciences. 2010; 2(2):70-76.

Nachigami et al. Isolation and Conparative Physico-Chemical Studies of Concanavalin A. Bulleting of Tokyo College of Domestic Science. 1978; 2: 45-50.

Yavuz et al. Concanavalin A Binding on PHEMA Beads and Their Interactions with Myeloma Cells. Journal of Macromolecular Science. 2009;46:163-169.

* cited by examiner

1) Preparation of Con A-linked magnetic bead

Streptavidin coted magnetic bead     Biotinylated Con A

2) Separation and concentration of virus

3) Detection of virus (RT-PCR)

Example of application of virus concentration method to food (lettuce)

| classification | pretreatment method using Con A | conventional pretreatment method |
| --- | --- | --- |
| eluent | 1% Con A aqueous solution | 100 mM Tris-HCl,<br>50 mM glycine,<br>1% beef extract, pH9.5 |
| ppt. method | acetone precipitation method | PEG precipitation method |
| rxn. time | 10 min | 10 min |
| results | $10^{-1}$ $10^{-2}$ $10^{-3}$<br> | $10^{-1}$ $10^{-2}$ $10^{-3}$<br> 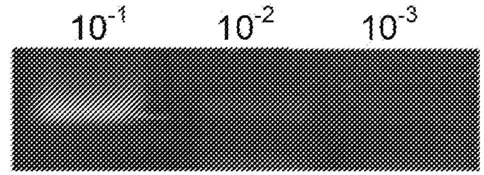 |

FIG. 8

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: primer for Hepatitis A Virus

<400> SEQUENCE: 1
tggtttgcca tcaacactga gg                                              22

<210> SEQ ID NO 2
<211> LENGTH: 23
<212> TYPE: DNA
<213> ORGANISM: Artificial Sequence
<220> FEATURE:
<223> OTHER INFORMATION: primer for Hepatitis A Virus

<400> SEQUENCE: 2
acccaaggag tatcaacggc aag                                             23

<210> SEQ ID NO 3
<211> LENGTH: 20
<212> TYPE: DNA
<213> ORGANISM: Artificial Sequence
<220> FEATURE:
<223> OTHER INFORMATION: primer for  Norovirus

<400> SEQUENCE: 3
tggacgagrg ggccyaayca                                                 20
```

```
-continued

<210> SEQ ID NO 4
<211> LENGTH: 21
<212> TYPE: DNA
<213> ORGANISM: Artificial Sequence
<220> FEATURE:
<223> OTHER INFORMATION: primer for  Norovirus

<400> SEQUENCE: 4
ggayctcatc cayctgaaca t                                              21
```

METHOD FOR THE CONCENTRATION AND DETECTION OF VIRUS

SEQUENCE LISTING

The present application contains a Sequence Listing which has been submitted in ASCII format via EFS-Web and is hereby incorporated by reference in its entirety. Said ASCII copy, created on Sep. 10, 2014, is named 96403_ST25.txt and is 998 bytes in size.

TECHNICAL FIELD

The present invention relates to an economic method of concentrating virus and detecting the virus. The method particularly includes efficiently concentrating a virus sample solution having low virus concentration within a short time, and detecting the virus from the concentrated virus sample.

BACKGROUND ART

As defined in Article 4 of the Korean Food Sanitary Law which provides basis for prohibition against marketing of hazardous foods and the like, the term "hazardous substance or hazard" refers to a biological, chemical or physical contaminants or condition which may have potency to cause an adverse effect in human health. Other foreign substances or deterioration having no direct impact on the consumer's health is not considered hazardous. Hazards or hazardous substance can be classified as shown in Table 1 below.

TABLE 1

| Hazards | Details |
| --- | --- |
| Biological hazards | *Bacillus cereus, Clostridium perfringens, Clostridium botulinum, Campylobactor jejuni, Escherichia coli* O157:H7, *Listeria monocytogenes, Salmonella* spp., *Yersinia enterocolitica, Staphylococcus aureus, Vibrio parahaemolyticus,* viruses, parasites, etc. |
| Chemical hazards | Natural toxins (fungal toxin, shell toxin and mushroom toxin), animal drug residue, hormones, pesticide residue, endocrine disruptors (environmental hormones), heavy metals (mercury, lead and cadmium), allergens, unapproved food additives, chemicals (acrylamide, etc.) that occur during processing and storage, radioactivity, etc. |
| Physical hazards | Foreign substances, glass, metals, stones, twigs, wood leaves, wood, rust, noxious insects, jewels, accessories, hair, etc. |

The present invention particularly relates to the detection of biological hazards, which include microorganisms such as fungi, bacteria, viruses and parasites. Biological hazards can be introduced into a warehouse during the production and distribution of food, and can also contaminate food as included in a food produce itself a warehouse environment, and a production and processing equipment, or by unsafe handling.

Food poisoning outbreaks caused by hazards in foods derived from agricultural, marine and livestock products have a serious impact on public health. The domestic economic loss caused by the food poisoning outbreaks reaches to about 1.3 trillion Won (Korean currency) per year due to the absence of a suitable method and system for early detection of the hazards. Among them, microbiological food poisoning may be most frequently caused by bacteria and virus, and viral food poisoning accounts for about 34-40% of microbial food poisoning and causes an economic loss of about 4 billion Won (Korean currency).

Although the sanitary condition of the modern urban environment has been improved, food poisoning caused by norovirus infection has been increased recently, and the number of death associated with norovirus infection in Japan and Europe was recorded as 6 and 12, respectively, in the year of 2012. Moreover, the US Centers for Disease Control and Prevention reported that norovirus infection caused a total of 348 outbreaks during a period from 1996 to 2000.

In addition, it has been also reported that the rate of positive antibody test against hepatitis A virus (HAV) in young and adults has decreased, and accordingly, the cases of HAV infection virus have increased. Hepatitis A virus disease is a highly infectious and waterborne disease and may cause an acute inflammatory liver condition. This virus infects humans through faces or via an oral route, and it is estimated that about 1.5 million cases of HAV infection occur worldwide annually. In South Korea, hepatitis A disease has been designated as an infectious disease since 2000, and the number of HAV infection cases has increased from about 100 cases in 2001 to about 7,655 cases in 2010.

According to this tendency, norovirus and hepatitis A virus infection have been designated as group 1 infectious diseases since 2010 and the cases of those viral infections have been reported via a mandatory surveillance system to the Korea Centers for Disease Control and Prevention.

Meanwhile, detection of hazardous virus in agricultural product samples such as fruits and vegetables have been reported in Korea and other countries. When contaminated food and underground water infected with a virus is consumed without being cooked or boiled, viral infection may occur. For example, infection with norovirus and hepatitis A virus may be particularly associated consuming a raw oyster. In Table 2, the major sources of norovirus and hepatitis A virus and prevention methods thereof are listed.

TABLE 2

| | Characteristics and initial symptoms (latent stage) | Sources that cause infection | Prevention |
| --- | --- | --- | --- |
| Norovirus | proliferates only in human intestinal tracts viable in natural environments for a long | water or food contaminated with human feces secondary infection | restraint of shells such as oysters, produced in contaminated sea areas shells should be |

TABLE 2-continued

| | Characteristics and initial symptoms (latent stage) | Sources that cause infection | Prevention |
|---|---|---|---|
| | period of time there is no antiviral agent or vaccine occurs mainly in winter nausea, vomiting, diarrhea, abdominal pain, and headache (24-48 hours) | by a person infected with norovirus. | consumed after heating (at 85° C. or higher for 1 minute or more thorough management of personal sanitation use of tap water for pretreatment of vegetables thorough management of contamination sources (toilet, etc.) around facilities that use underground water. |
| Hepatitis A virus | Fever, nausea, vomiting, abdominal pain, fatigue, and jaundice (10-50 days) | contaminated drinking water food that came into contact with a person infected with hepatitis A virus water, strawberries, mollusk, fishes and shells. | cooking at recommended temperature all shells should be eaten boiled thorough management of personal sanitation |

Thus, a method for rapid detection of virus to assess viral contamination in food from agricultural, marine and livestock products and assure safe food supply to consumers may prevent the above-described socioeconomic loss.

Typically, food poisoning virus can be diagnosed by an enzyme immunoassay or molecular biological assay using a monoclonal or polyclonal antibody. In addition, a diagnostic method based on chip technology has been developed recently.

For detection of virus in food, at first, virus recovered from food samples can be obtained by eluting and concentrating the virus in the eluate is performed before the detecting the virus. Elution of virus may be performed using various elution buffers depending on analysis agencies. The eluted virus is subsequently concentrated using an immunomagnetic capture, an organic flocculation or a PEG (polyethylene glycol) precipitation method. The immunomagnetic capture method may reduce the time for concentrating virus, but may be an expensive method due to use of an expensive antibody. Organic flocculation and the PEG precipitation methods may have disadvantages as a process for concentrating the virus due to time-consuming and complicated procedures, which further cause increase in loss of virus, thus reducing the sensitivity of detection.

Bacterial waterborne diseases such as typhoid fever, cholera, and bacterial and amoebic dysentery have greatly decreased since safe drinking water, sanitation systems and methods have been provided. However, protozoa cannot be easily removed in a water purification process due to high resistance to chlorine disinfection. For this reason, the incidence of diseases caused by *Giardia* and *Cryptosporidium* may be still problematic. In addition, a single unit of waterborne virus may cause infection, and thus contamination with the virus may occur without detection of an indicator microorganism. Infection with virus occurs when contaminated water is consumed without treatment or with insufficient treatment from a private or simplified water purification system. For example, in underground water, various hazardous substances are detected mostly due to the contamination with environmental pollutants. Particularly, norovirus that is contagious through excretes of infected patients is in substantially small size such that it easily penetrates soil. Further, norovirus can be viable for a long period of time even in underground water that is maintained at low temperature. Accordingly, there is still a need for providing drinking water free from biological hazards such as virus by methods of detecting viruses in a short time.

SUMMARY

In one aspect, the present invention provides a method for concentrating virus, comprising the steps of: adding a Concanavalin A to a sample solution containing a virus and reacting the added Concanavalin A with the virus to form a virus—Concanavalin A conjugate; and separating the virus-Concanavalin A conjugate from the sample solution. In another aspect, the present invention provides a virus probe comprising Concanavalin A linked covalently to a support. In still another aspect, the present invention provides a method for detecting virus, comprising steps of: preparing a sample solution containing a virus from a sample; concentrating the virus in the sample solution by adding a Concanavalin A to the sample solution and reacting the added Concanavalin A with the virus to form a virus—Concanavalin A conjugate, and separating the virus-Concanavalin A conjugate from the sample solution, thereby obtaining a virus concentrate; and detecting the virus in the virus concentrate. In a further aspect, the present invention provides a water purification method comprising passing water containing a virus through a Concanavalin A-linked resin. The above and other aspects of the invention will be detailed below.

BRIEF DESCRIPTION OF THE DRAWINGS

FIG. 8 shows a comparison of the efficiency with which hepatitis A virus is detected in a food material (lettuce) according to an exemplary embodiment of the present invention.

DETAILED DESCRIPTION

Figure 1A:
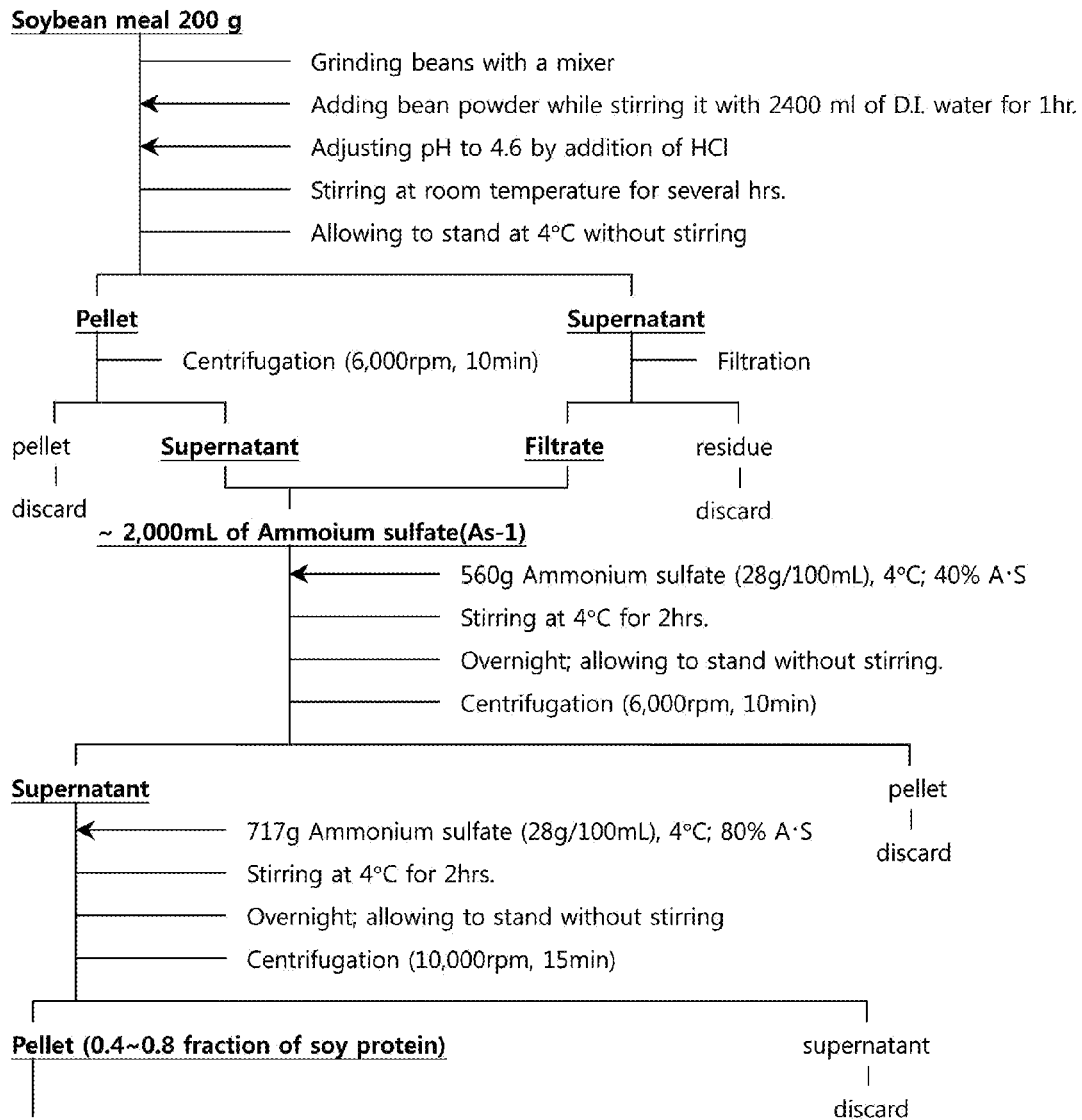
FIGS. 1A-1B show exemplary processes for preparing a Con A crude protein according to exemplary embodiments of the present invention.
Figure 1B:
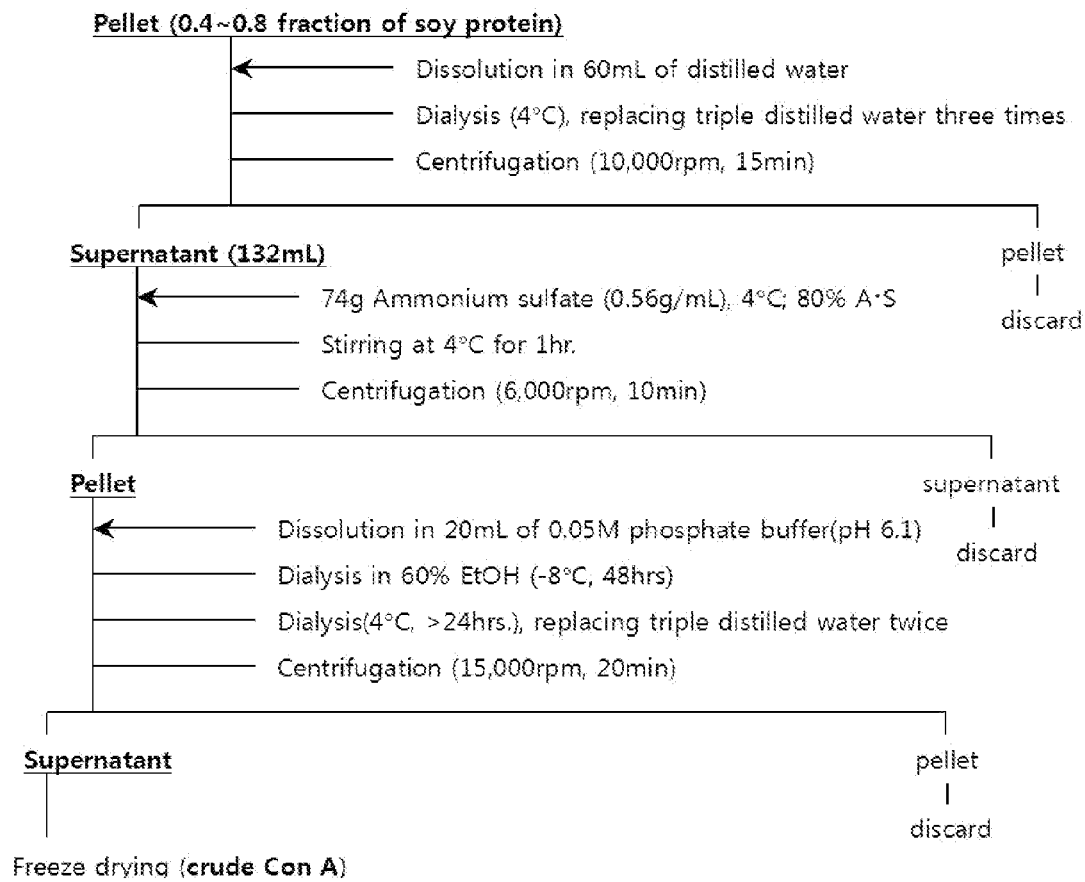

In one aspect, the present invention provides a method of concentrating and detecting virus within a short time using conventional equipment and chemicals. In certain aspect, a method of preparing a protein to which a virus can bind is provided, such that the method may be economical and effective for concentrating viruses from foods. In yet certain aspect, the present invention provides a method of preparing a virus probe that can be used for concentrating and detecting virus. Moreover, in another aspect, the present invention may further provide an efficient water purification method in which virus is effectively removed from water.

In one embodiment, the present invention provides a method for concentrating virus. The method comprises the steps of: (A) adding Concanavalin A (Con A) to a sample solution containing a virus and reacting the added Concanavalin A with the virus in the sample solution to form a virus-Concanavalin A conjugate; (B) separating the virus-Concanavalin A conjugate from the sample solution. In particular, Con A which binds specifically to virus can be used to concentrating the virus.

In one embodiment, provided is a novel method for rapidly detecting virus. In particular, Con A which binds specifically to virus can be used to concentrating and detecting virus.

Concanavalin A or Con A, as used herein, is a protein which may be commercially available as a purified reagent. However, Con A may be expensive as it costs hundreds of thousands of Won (Korean currency) per gram. When large numbers of samples and repeated experiments are required for, for example, detecting virus in each food sample, not for research purposes in laboratories, an economical and local source of Con A may be required. For the purpose of concentrating virus according to certain exemplary embodiments of the present invention, Con A as crude protein from foods may also be used instead of the purified reagent. The crude protein sample, as disclosed herein, may have a substantial content of Con A which may be sufficient to concentrate virus.

Accordingly, in certain aspect, a method for preparing a crude protein sample having a high content of Con A is provided. In particular, the method for preparing the crude protein sample having a high content of Con A may comprise the steps of: (a) extracting ground beans with water to obtain an aqueous extract; (b) precipitation with ammonium sulfate at a saturation degree of about 0.4 to 0.8, and collecting a pellet fraction precipitated from the aqueous extract (c) removing the ammonium sulfate from the pellet fraction. As used herein, the term "saturation degree" refers to the concentration of ammonium sulfate in a solution.

In certain exemplary embodiments of the present invention, reacting the added Concanavalin A with the virus to form a virus—Concanavalin A conjugate may be performed for about 5 minutes to 1 hour. When the reaction time is less than 5 minutes, the binding between Con A and virus may not be sufficient, and thus the efficiency of concentration may be reduced. Generally, as the reaction time increases, the efficiency of concentration may increase accordingly. However, when the reaction time is greater than 1 hour, the effect will not greatly increase, although other problems do not arise. In yet certain exemplary embodiments, the reaction time may be from about 10 to about 30 minutes.

In certain exemplary embodiment, the virus which is subjected to concentrating and detecting may be, but not limited to, norovirus and hepatitis A virus.

In certain exemplary embodiments, separating the virus-Con A conjugate from the sample solution may be performed using a suitable method selected from various methods in the art depending on the intended use. For example, the virus-Con A conjugate can be recovered by adding a water-miscible organic solvent such as acetone to the reaction solution to precipitate the virus-Con A conjugate. Alternatively, the virus-Con A conjugate can be separated by preparing a virus probe comprising Con A linked to a magnetic bead or resin, adding and reacting the prepared virus probe comprising Con A in step (A), and recovering the probe. The Con A that is linked to the magnetic bead or resin in an exemplary embodiment of the present invention may be a purified Con A, crude Con A extracted from foods, or mixtures thereof without limitation, because no significant different results are obtained from those.

In other aspect, the present invention provides a virus probe comprising Con A linked covalently to a support. The support may be a solid material that can immobilize Con A, and any material which has a functional group capable of forming a bond with Con A may be used as the support. In an exemplary embodiment of the present invention, a magnetic bead or a resin may be used as the support. In addition, a paper or a porous carrier may also be used as the support. When the virus probe comprises a magnetic bead as the support, the virus probe can be easily recovered by a magnet or filtration. When a resin or a paper is used as the support, it can be easily recovered by filtration. Any person skilled in the art would easily prepare the virus probe comprising Con A by the use of conventional technology as describe in the art (e.g. Shan S. Wong and David M. Jameson "Chemistry of protein and nucleic acid cross-linking and conjugation" CRC press, 2011).

In one embodiment, a method for detecting virus is provided in the present invention. The method comprises steps of: The method comprises steps of: (A) preparing a sample solution containing a virus from a sample; (B) concentrating the virus in the sample solution by adding a Concanavalin A to the sample solution, reacting the added Concanavalin A with the virus to form a virus—Concanavalin A conjugate and separating the virus-Concanavalin A conjugate from the sample solution, thereby obtaining a virus concentrate; and (C) detecting the virus in the virus concentrate.

If the sample is a solid sample such as vegetables, the sample solution is prepared by eluting virus from the solid sample. In certain embodiments, a Con A solution may be used as a virus eluent solution to elute virus while reacting Con A with the virus. In yet certain embodiments, a crude protein may also be used as Con A.

If the above-described virus probe is used as a Con A sample, virus can be detected either after eluting the virus from the virus probe or in a state in which the virus is bound to the probe. Elution of virus from the probe may be performed as described in the art (e.g., Sousa et al., Antibody cross-linking and target elution protocols used for immunoprecipitation significantly modulate signal-to noise ratio in downstream 2D-PAGE analysis, Proteome Science 2011, 9(45)).

In certain exemplary embodiments, detecting the virus in the virus concentrate can be performed by a suitable method known in the art. The detecting method may be, but not limited to, a direct counting method using an electron microscope, an immunoenzymatic method using an antibody specific to a viral antigen, or a gene detection method using polymerase chain reaction (PCR), depending on the intended use and the characteristics of the virus.

In another aspect, the present invention also provides a water purification method comprising passing water through a Con A-linked resin. As provided in the Examples of the present invention, substantially small amount of virus in water can be effectively removed by passing the water through a Concanavalin A (Con A)-linked resin.

EXAMPLES

Figure 2A:
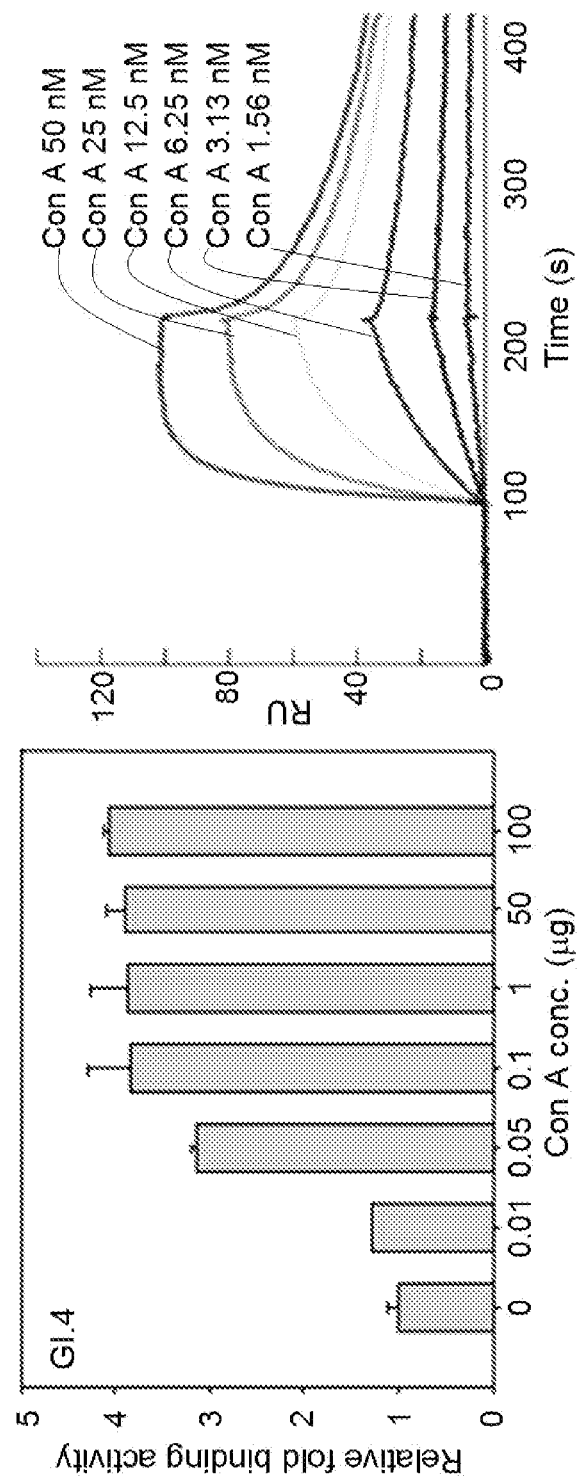
FIGS. 2A to 2C are graphs showing the binding affinity between con A and virus.
Figure 2B:
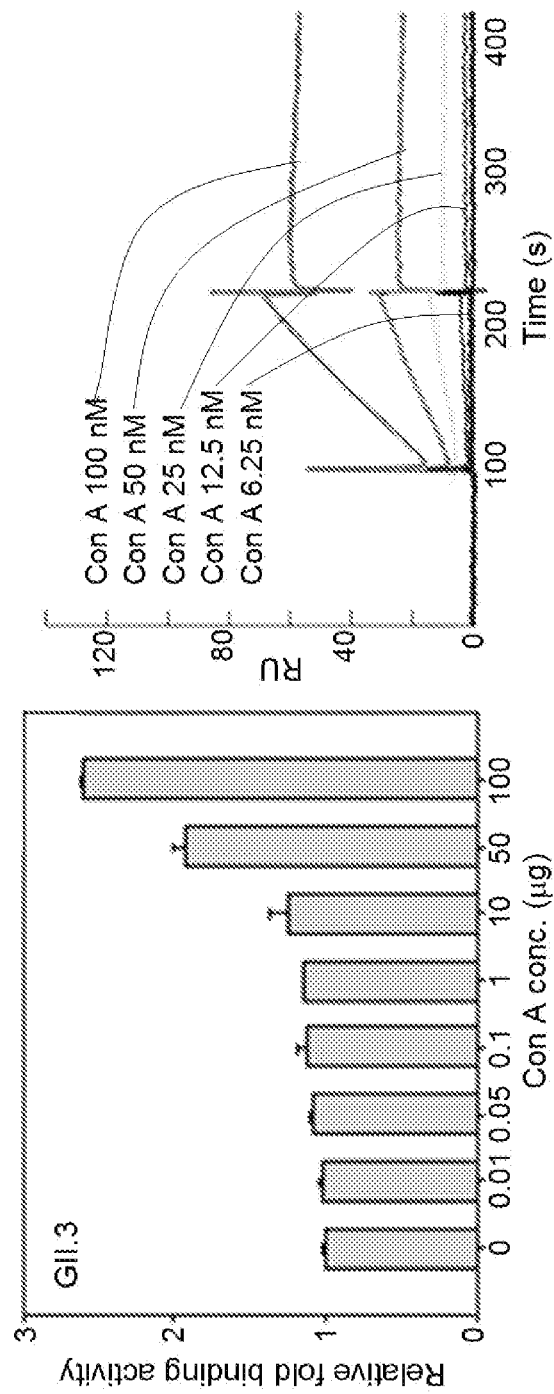
Figure 2C:
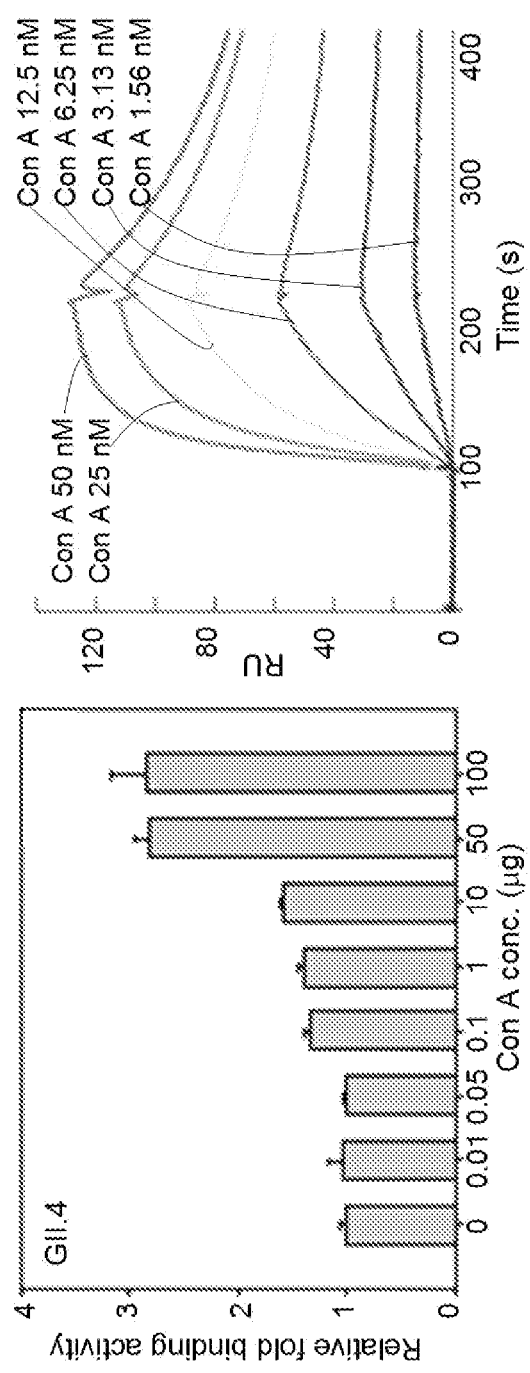
Figure 3A:
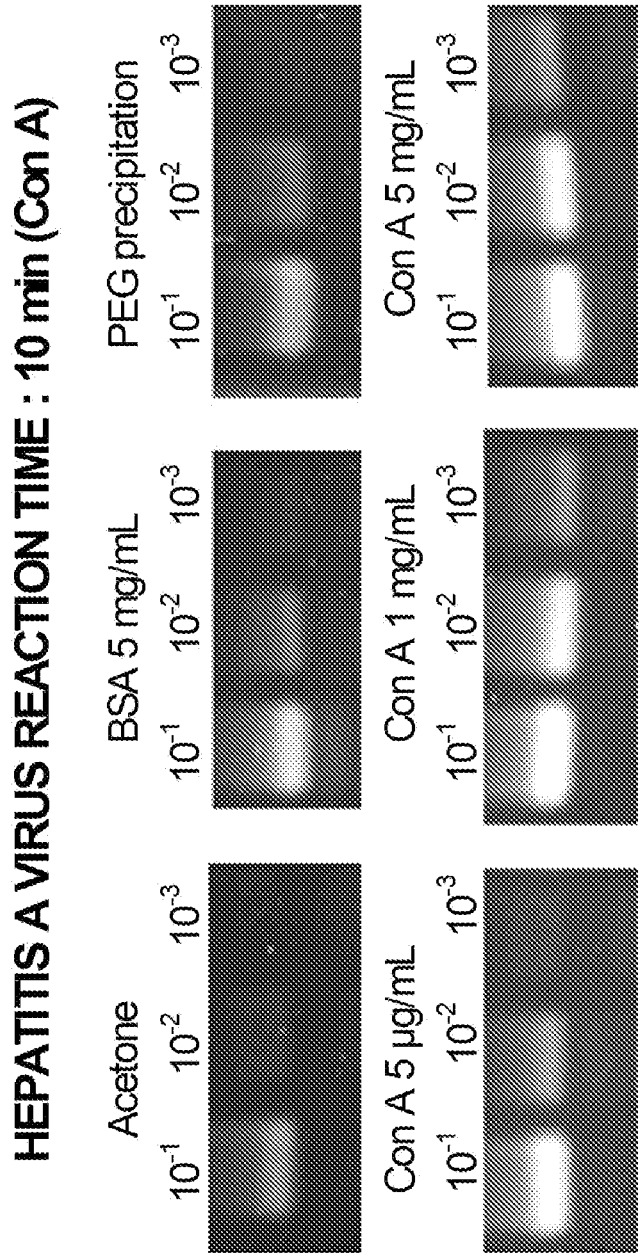
FIGS. 3A and 3B show electrophoresis results after RT-PCR, and represent the efficiency of concentrating hepatitis A virus in each method, using purified Con A (FIG. 3A) and crude Con A (FIG. 3B).
Figure 3B:
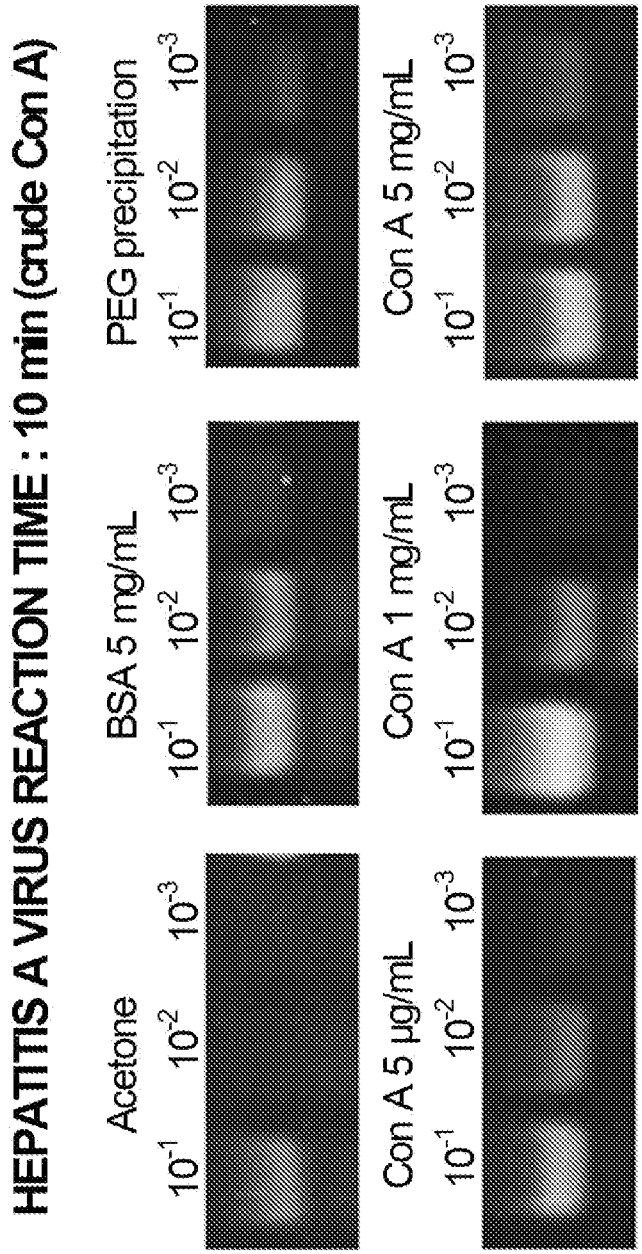
Figure 4A:
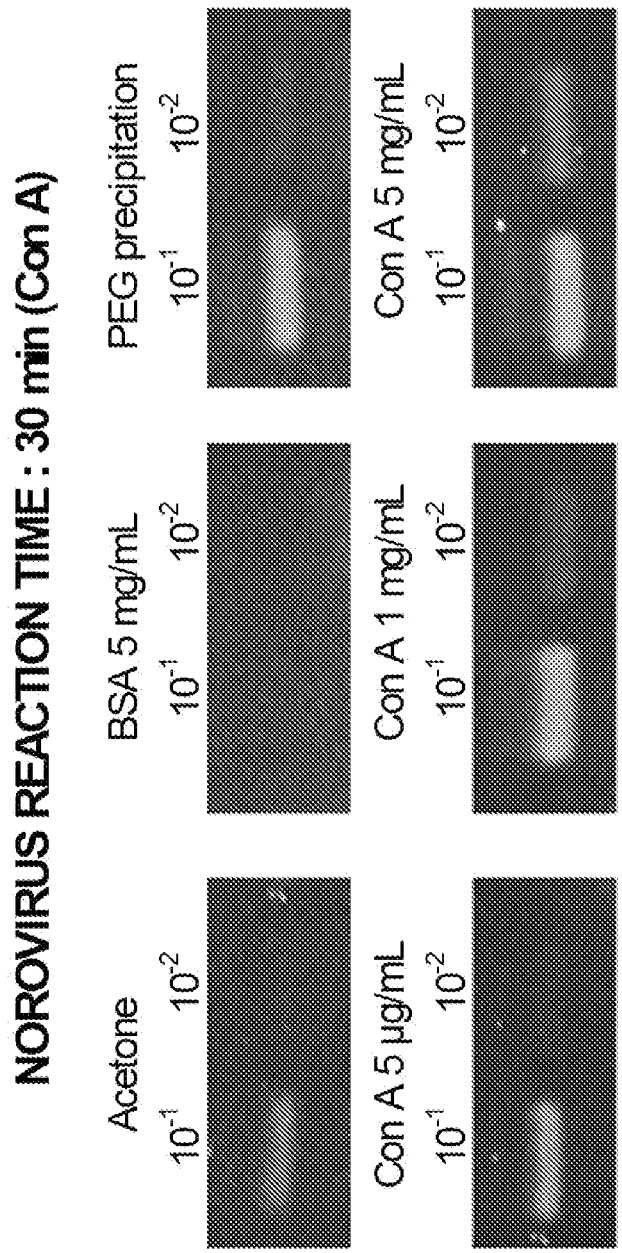
FIGS. 4A and 4B show electrophoresis results after RT-PCR, and represent the efficiency of concentrating norovirus in each method, using purified Con A (FIG. 4A) and crude Con A (FIG. 4B).
Figure 4B:
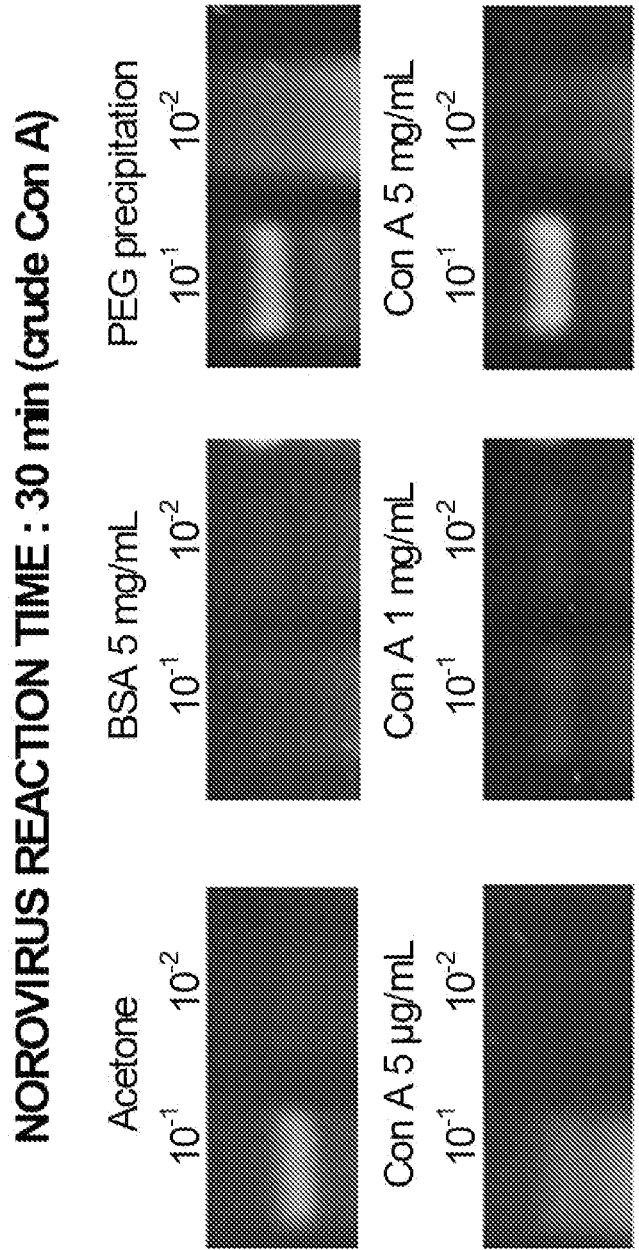
Figure 5:
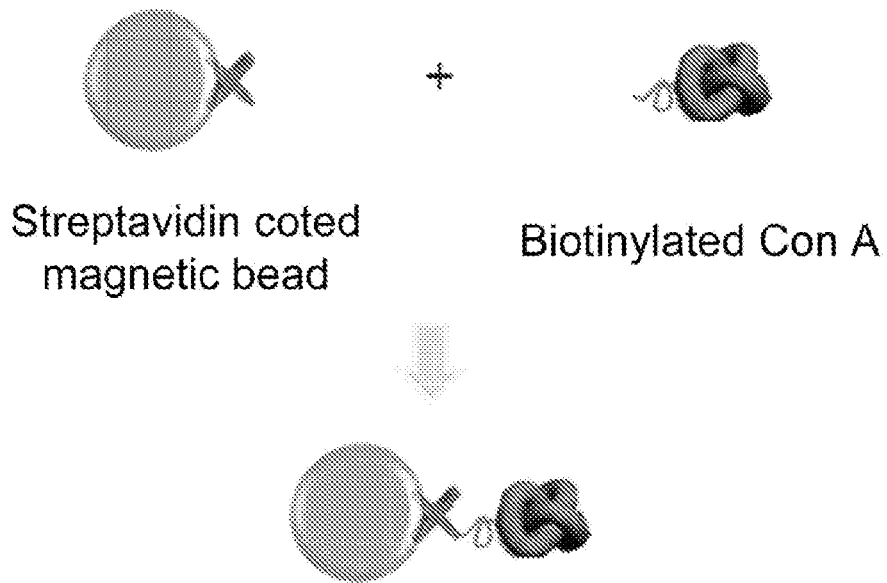
FIG. 5 is a schematic illustration of an exemplary method for detecting virus according to an exemplary embodiment of the present invention.
Figure 5:

Hereinafter, the present invention will be described in further detail with reference to the accompanying drawings and examples. It is to be understood, however, that these drawings and examples are for illustrative purposes only and are not intended to limit the technical scope of the present invention. Moreover, those skilled in the art will appreciate that various changes and modifications based on this illustration are possible without departing from the technical spirit of the present invention.

Example 1

Separating Virus-Bound Crude Protein 200 g of Jack-beans were ground with a mixer, and then stirred with 2,400 mL of distilled water for 1 hour. Then, the solution was adjusted to a pH of about 4.6 using HCl and stirred at room temperature for 2 hours, and subsequently the reaction solution was allowed to stand overnight at 4° C. without stirring. Then, the supernatant of the reaction solution was filtered through a Whatman paper filter (No. 4), and the pellet was centrifuged at 6,000 rpm for 10 minutes. The supernatant of the centrifugation was combined with the filtrate, thereby obtaining about 2 liters of an extract.

The obtained extract was stirred at 4° C. and 560 g of ammonium sulfate was added to the extract so that the saturation degree of ammonium sulfate reached 0.4. Subsequently, the solution was stirred at 4° C. for 4 hours, and then allowed to stand overnight without stirring. Next, the solution was centrifuged at 6,000 rpm for 10 minutes, and about 2,560 mL of the supernatant was collected. The collected supernatant was stirred at 4° C. and 717 g of ammonium sulfate was additionally added to the supernatant so that the saturation degree of ammonium sulfate reached 0.8. Thereafter the solution was stirred for 2 hours, and then allowed to stand overnight. On the next day, the solution was centrifuged at 10,000 rpm for 15 minutes, the supernatant was discarded, and the pellet was collected and redissolved in 60 mL of distilled water.

The pellet solution (bean protein fraction) obtained using ammonium sulfate at a saturation degree of about 0.4-0.8 according to the above-described method was dialyzed SPECTRA/POR® 6 (Standard Grade Regenerated Cellulose membrane) (Spectrum Laboratories, USA) with distilled water to remove remaining ammonium sulfate. For additional purification, the dialyzed solution was centrifuged at 10,000 rpm for 15 minutes, and about 132 mL of the supernatant was collected.

74 g of ammonium sulfate was added to the supernatant so that the saturation degree reached 0.8, and the resulting bean extract was stirred at 4° C. for 1 hour, and then centrifuged at 6,000 rpm for 10 minutes. The pellet resulting from the centrifugation was dissolved in 20 mL of 0.05 M phosphate solution (pH 6.1) and dialyzed in 60% (v/v) ethanol at −8° C. for 48 hours. Then, the 60% ethanol was removed, and the remaining solution was dialyzed with triple distilled water for 24 hours. The dialyzed solution was centrifuged at 15,000 rpm for 20 minutes, and the supernatant was freeze-dried, thereby separating about 0.43 g of a crude protein containing Concanavalin A (Con A) from beans.

FIG. 1 is a flowchart showing a process for separating a Con A-containing crude protein from beans.

Example 2

Examination of Binding Efficiency Between Con A and Virus

The binding affinity between Con A and virus was analyzed by ELISA and a Surface Plasmon Resonance (SPR) assay. The viral species, GI.4, GII.3 or GII.4 norovirus, was received from the Gwangju Institute of Health and Environment (Korea) and used for the assay.

In the ELISA assay, 50 μL of Con A was seeded into each well of a 96-well plate at concentrations of 0, 0.01, 0.05, 0.1, 1, 50 and 100 [ig/mL and coated at 4° C. for 12 hours. Next, each well was washed three times with PBS containing 0.02% TWEEN® 20 (polysorbate 20) (Sigma, USA), and then preincubated with PBS solution containing 5% non-fat dry milk (SKI400, Bioshop, Canada) for 1 hour. Thereafter, the norovirus was allowed to react with Con A at room temperature for 2 hours and washed three times with PBS containing 0.02% TWEEN® 20 (polysorbate 20). Then, each well was incubated with a 1000-fold diluted primary antibody (Anti-Norovirus Capsid protein VP1 antibody, ab92976, Abcam, UK) in 5% non-fat dry milk in PBS solution for 1 hour and washed with PBS containing 0.02% TWEEN® 20 (polysorbate 20). Then, each well was incubated with a 2000-fold dilution of secondary antibody (Polyclonal Goat Anti-Rabbit Immunoglobulins/HRP, P0448, Dako, USA) in 5% non-fat dry milk in PBS solution for 1 hour. Then, o-phenylenediamine (OPD) substrate (P8287, Sigma) was added to each well, which was then incubated at room temperature for 20 minutes, and the reaction was quenched using 0.5 M $H_2SO_4$ solution. Next, the absorbance of each well was measured at 495 nm. The left figures in FIGS. 2A to 2C show the results of ELISA for each GI.4, GII.3 or GII.4 norovirus species. As can be seen therein, as the concentration of Con A increased, the detection of norovirus increased, and a significant value was shown at a concentration of at least about 50 μg/mL.

The Surface Plasmon Resonance (SPR) assay was performed using a Biacore 2000 SPR biosensor (GE, USA). Specifically, a CM5 chip (carboxymethylated dextran surface chip, Biacore, Inc., USA) was activated with N-ethyl-N'-(3-dimethylaminopropyl)-carbodiimide hydrochloride (EDC) and N-hydroxysuccinimide (NHS) according to the manufacturer's manual. Then, GI.4, GII.3 or GII.4 norovirus was injected such that about 350 response units (RU) were immobilised onto the chip, and 1 M ethanolamine solution was injected to block unreacted groups. Each Con A (Sigma-Aldrich, USA) aliquot diluted at various concentrations of about 0.25-100 nM was injected into the chip at a rate of 20

μL/min for 2 minutes. The right figures in FIGS. 2A to 2C show a plasmon resonance spectrum for each GI.4, GII.3 and GII.4 norovirus species, respectively. Using BIA evaluation ver. 3.2 software, association rate ($K_{on}$) and dissociation rate ($K_{off}$) of each norovirus species were calculated, and each equilibrium dissociation constant ($K_d$; $K_{off}/K_{on}$) was calculated therefrom. It could be seen that the equilibrium dissociation constants of GI.4, GII.3 and GII.4 noroviruses were about $4.47 \times 10^{-9}$, $4.62 \times 10^{-9}$ and $2.19 \times 10^{-9}$, respectively, suggesting that the three types of norovirus all have substantial binding affinities for Con A.

Example 3

Concentrating Norovirus and Hepatitis A Virus Using Con A or Con A-Containing Crude Protein Norovirus and hepatitis A virus were concentrated by methods as follows using Con A or the Con A-containing crude protein prepared in Example 1. In particular, GII.4 norovirus was used in the following experiment.

1) Concentrating Virus by Precipitation (1) Method of Concentrating Virus

Con A (Sigma-Aldrich, USA) or the crude protein prepared in Example 1 was added to $10^4$ $TCID_{50}$/mL of a hepatitis A virus sample (VR-1402, ATCC, USA) to make each final protein concentration of 0, 0.5, 1 or 5 mg/mL and allowed to react for 10 minutes. Then, acetone stored at −20° C. was added in 6-fold amount of the sample, and the solution was stirred, and then centrifuged at 2,000 rpm for 3 minutes. The supernatant was discarded, and the concentrated protein was collected. The collected protein was washed with 90% cold acetone and centrifuged under the same conditions as above. The supernatant was removed, and the pellet was dried for 5 minutes, thereby obtaining a concentrated hepatitis A virus pellet. As a control, a concentrated hepatitis A virus pellet was obtained in the same manner as described above, except that bovine serum albumin (BSA) (BioShop, Canada) was added instead of Con A at a concentration of 5 mg/mL and allowed to react for 10 minutes.

For comparison with a method in the related art, a virus concentrate was prepared by the PEG precipitation method. For example, a two-fold amount of PEG solution (16% PEG 6000 (Sigma Chemical Co., USA) containing 0.525 M NaCl (BioShop, Canada) in a two-fold volume of was added to a hepatitis A virus sample and allowed to react at 4° C. for 10 minutes. The reaction solution was centrifuged at 2,000 rpm for 3 minutes, and the supernatant was removed, thereby obtaining a hepatitis A virus concentrate in the form of a pellet. In the typical PEG precipitation method, the reaction is performed for 4-6 hours, but for comparison with the method of the present invention which is capable of concentrating virus within a short time, the same reaction time was applied as used in the PEG precipitation method.

For a norovirus sample (Gwangju Institute of Health and Environment, South Korea; 100 RT-PCR units/mL), a concentrated norovirus pellet was obtained as described with respect to the preparation of the hepatitis A virus concentrate, except that the norovirus sample was reacted with Con A, BSA or PEG for 30 minutes.

(2) Detecting Virus from Concentrated Sample

Each of the pellets prepared in Example 3-1-(1) was suspended in 200 μL of TE solution (10 mM Tris-Cl, 1 mM EDTA, pH 8.0), and then 10-fold diluted. Each of the dilutions was subjected to RT-PCR and electrophoresis to detect oligonucleotide fragments from hepatitis A virus or norovirus. The results are shown in FIGS. 3 and 4. FIG. 3A shows the results of detecting hepatitis A virus using Con A; FIG. 3B shows the results of detecting hepatitis A virus using the crude protein prepared in Example 1; FIG. 4A shows the results of detecting norovirus using Con A; and FIG. 4B shows the results of detecting norovirus using the crude protein prepared in Example 1.

As primers for detection of hepatitis A virus, HAV_VP1_F (SEQ ID NO: 1, 5'-TGG TTT GCC ATC AAC ACT GAG G-3') and HAV_VP1_R (SEQ ID NO: 2, 5'-ACC CAA GGA GTA TCA ACG GCA AG-3') were used, and as primers (Bioneer, South Korea) for detection of norovirus, Noro_Mon431_F (SEQ ID NO: 3, 5'-TGG ACI AGR GGI CCY AAY CA-3') and Noro_Mon 433_R (SEQ ID NO: 4, 5'-GGA YCT CAT CCA YCT GAA CAT-3') were used.

PCR for detection of each virus was performed under the following conditions:

PCR for detection of hepatitis A virus: 30 cycles, each consisting of denaturation at 94° C. for 30 sec, annealing at 57° C. for 30 sec, and extension at 72° C. for 30 sec, and final extension at 72° C. for 10 minutes.

PCR for detection of norovirus: 40 cycles, each consisting of denaturation at 94° C. for 30 sec, annealing at 60° C. for 30 sec, and extension at 72° C. for 30 sec, and final extension at 72° C. for 10 minutes.

As can be seen in FIG. 3A, the efficiency of concentration of hepatitis A virus was about 10 times higher when 0.5 mg/mL of Con A was added, compared to when no Con A was added, and the efficiency of concentration increased as the amount of Con A added increased. Also, the results of comparison using a densitiometer indicated that the efficiency of concentration was 0.4 times lower when BSA, a negative control protein of Con A, was added at a concentration of 5 mg/mL, compared to when Con A was added at a concentration of 0.5 mg/mL. The efficiency of concentration in the conventional PEG concentration method was 0.5 times lower compared to when 0.5 mg/mL of Con A was added, suggesting that the efficiency of concentration is high even when Con A is used at a low concentration of 0.5 mg/mL.

FIG. 3B shows the efficiency with which virus is concentrated using the crude protein prepared in Example 1, instead of the purified Con A. As can be seen therein, when the crude protein was used at a concentration of 5 mg/mL, the efficiency of concentration was similar to when purified Con A was used, and the efficiency of concentration was significantly high compared to that in the conventional PEG precipitation method.

FIG. 4A shows the efficiency with which norovirus is concentrated. As can be seen therein, norovirus was effectively concentrated when Con A was used, compared to when the conventional PEG precipitation method was used. In addition, the efficiency of concentration was lower when acetone alone was used, compared to when the negative control protein BSA was used. FIG. 4B shows the efficiency with which norovirus is concentrated using the crude protein prepared in Example 1. As can be seen therein, like the results for hepatitis A virus, the efficiency of concentration shown by the use of the crude protein was lower than that shown by the use of purified Con A, but was similar to that in the conventional PEG precipitation method.

2) Concentrating Virus Using Magnetic Bead (1) Preparing Con A-Linked Magnetic Bead A Con A-linked magnetic bead was prepared by reacting a streptavidin-coated magnetic bead with biotinylated Con A (concanavalin A) (FIG. 5).

Specifically, Con A (Sigma-Aldrich, USA) was biotinylated using the Biotin-XX microscale protein labeling kit (B30010; Molecular Probes, USA) according to the manufacturer's manual. Briefly, 100 μL of 1 mg/mL Con A solution and 100 μL of 1 M sodium bicarbonate were mixed with each other in a reaction tube (component C). Then, 1 μL of a solution prepared by adding 10 μL of ionized water to biotin-XX, SSE (component A) was added to the mixture and allowed to react at room temperature for 15 minutes. Next, biotinylated Con A was purified using the spin filter (component D) and purification resin (component E) included in the kit.

To 10 μg of the biotinylated con A prepared by the above method, 1 mg of a streptavidin-coated magnetic bead (10 mg/mL, M-280 streptavidin, 11206D; Invitrogen, USA) was added, and the mixture was allowed to react at room temperature for 1 hour. Then, the bead was recovered by magnetism and washed with PBS containing 0.02% TWEEN® 20 (polysorbate 20) (Sigma, USA), thereby preparing a Con A-linked magnetic bead.

(2) Concentrating Virus

In a sample tube containing the Con A-linked magnetic bead prepared in Example 3-2)-(1), 200 μL of a solution of $10^4$ $TCID_{50}$/mL of a hepatitis A virus sample (VR-1402, ATCC, USA) or a norovirus sample (Gwangju Institute of Health and Environment (South Korea), 100 RT-PCR units/mL) diluted to a concentration of $10^{-1}$-$10^{-4}$ was placed and allowed to react at room temperature for 10 minutes. After completion of the reaction, the magnetic bead was collected using a magnet and washed three times with 200 μL of PBS (Phosphate Buffered Saline; Biosesang, South Korea). The washed magnetic bead and 100 μL of PBS were suspended in a 1.5 ml tube, and the supernatant was removed.

In order to separate the virus conjugate bound to the magnetic bead, 50 μL of an eluent solution (50 mM Glycine, pH 2.8) was added to the tube containing the magnetic bead, and the content in the tube was neutralized to pH 7.5 using 100 mM Tris solution.

(3) Detecting Virus

Figure 6A:
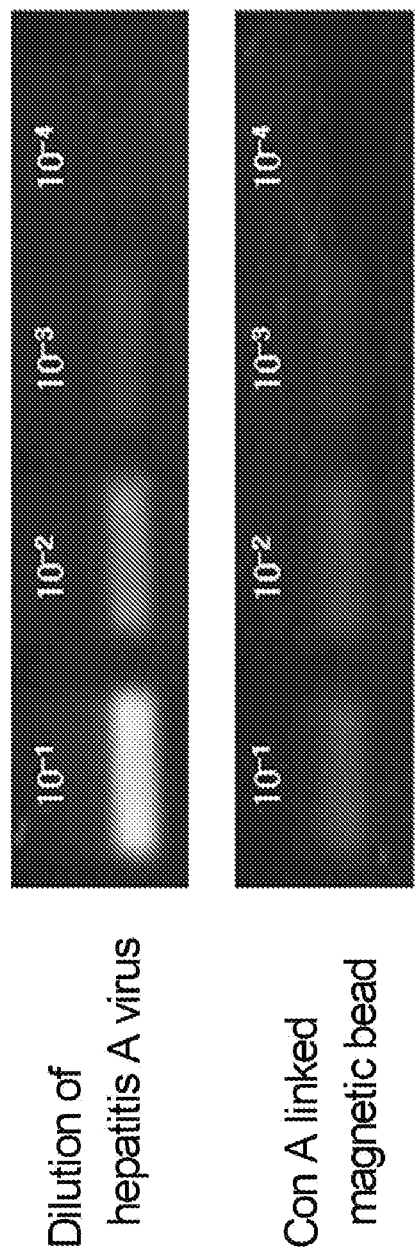
FIGS. 6A and 6B show electrophoresis results after RT-PCR and represent the efficiencies of concentrating norovirus and hepatitis A virus by the method of FIG. 5, respectively.
Figure 6B:
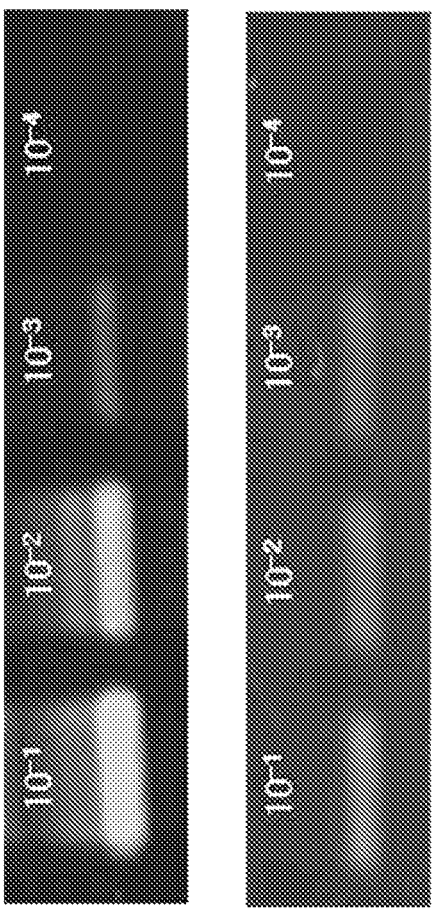

In each of the solutions eluted after concentration using the magnetic bead in Example 3-2)-(1) and the diluted virus solutions, the target virus was detected by electrophoresis after RT-PCR according to the method described in Example 3-1)-(2). FIGS. 6a and 6b shows electrophoresis photographs showing the results of detection of norovirus and hepatitis A virus.

As can be seen in FIGS. 6A and 6B, hepatitis A virus and norovirus were detected in the solutions diluted 1000-fold or less before concentration, and even when the Con A-linked magnetic bead was used, hepatitis A virus and norovirus could be detected by RT-PCR in the samples diluted 1000-fold (detection limit) or less.

3) Concentrating Virus Using Resin (1) Preparing Con A-Linked Resin

In order to activate the carboxyl group of resin, 0.5 g of an ion exchange resin (WK60L, Yiryoong Chemicals, Co., Ltd., South Korea) was added to a [volume] 30% EtOH solution containing 10 mg of EDC (N-ethyl-N'-(3-dimethylaminopropyl)carbodiimide hydrochloride) dissolved therein and was allowed to react for 10 minutes. After removing the supernatant, a [volume] 30% EtOH solution containing 10 mg of con A dissolved therein was added to the residue and allowed to react for 12 hours. The resin was collected from the reaction solution and washed with [volume] 30% EtOH.

(2) Concentrating Virus

Norovirus was concentrated using the con A-linked resin prepared in Example 3-3)-(1). Specifically, 0.34 g of the con A-linked resin was packed into a column (80 mm×200 mm), and then 0.5 mL of a norovirus dilution (GII.4, 4.07×10²/mL) was allowed to run through the column, and the column was washed with 0.5 mL of PBS (Phosphate Buffered Saline; Biosesang, South Korea) containing 0.02% (v/v) TWEEN® 20 (polysorbate 20) (Sigma, USA). The filtrate and the resin were separately collected, and virus contained therein was qualitatively and quantitatively analyzed as described below.

(3) Detecting Virus

The virus dilution passed through the resin, and the virus contained in the resin, were qualitatively and quantitatively analyzed. For comparison, a virus dilution was passed through a non-Con A-linked resin in the same manner as described in Example 3-3)-(2), and the amount of virus contained in the filtrate passed through the resin and the amount of virus contained in the resin were analyzed.

Specifically, each of the virus dilution, the filtrate passed through the Con A-linked resin, and the resin collected after washing of the filtrate, was subjected to RT-PCR according to the method described in Example 3-1)-(2) and was electrophoresed on agarose gel. The gel was stained with ethidium bromide (EtBr), and the results are shown in FIG. 7b. The virus in the resin was analyzed after extraction with 0.5 ml of TRIZOL® (guanidinium thiocyanate-phenol-chloroform) (Invitrogen, Carlsbad, Calif., USA). As can be seen in FIG. 7b, norovirus was not detected in the virus dilution passed through the con A-linked resin column, but was detected in the collected resin. On the other hand, norovirus was detected in the virus dilution passed through the non-con A-linked resin column, but was detected in the collected resin.

For more detailed analysis, quantitative analysis was performed.

In order to obtain a standard curve for quantification, the RNA of norovirus was extracted and reverse-transcribed into cDNA. The RNA of norovirus was transcribed using the cDNA as a template and Noro_Mon431_F and Noro_Mon 433_R as primers. The cloned RNA was inserted into pTOP TA V2 (Enzynomics, EZ001S, South Korea) to prepare a plasmid, which was then diluted 10-fold and used as a standard sample for real-time RT-PCR.

A standard reaction solution used per reaction consisted of 2 tL of the cloned plasmid, 10 μL of SYBR® Premix Ex Taq (Tli RNase H Plus) (Takara, RR420A, Japan) and 0.5 μL of each of forward and reverse primers (10 pmol). The standard reaction solution was adjusted to a final volume of 20 μL with PCR grade water, and then subjected to RT PCR using a RT PCR machine (Takara, TP850, Japan). The PCR reaction was performed for 45 cycles, each consisting of 95° C. for 10 sec, 55° C. for 20 sec, and 72° C. for 30 sec. The amplified fluorescence value was measured once after reaction at 72° C. for 10 sec during each polymerase chain reaction cycle.

Figure 7A:
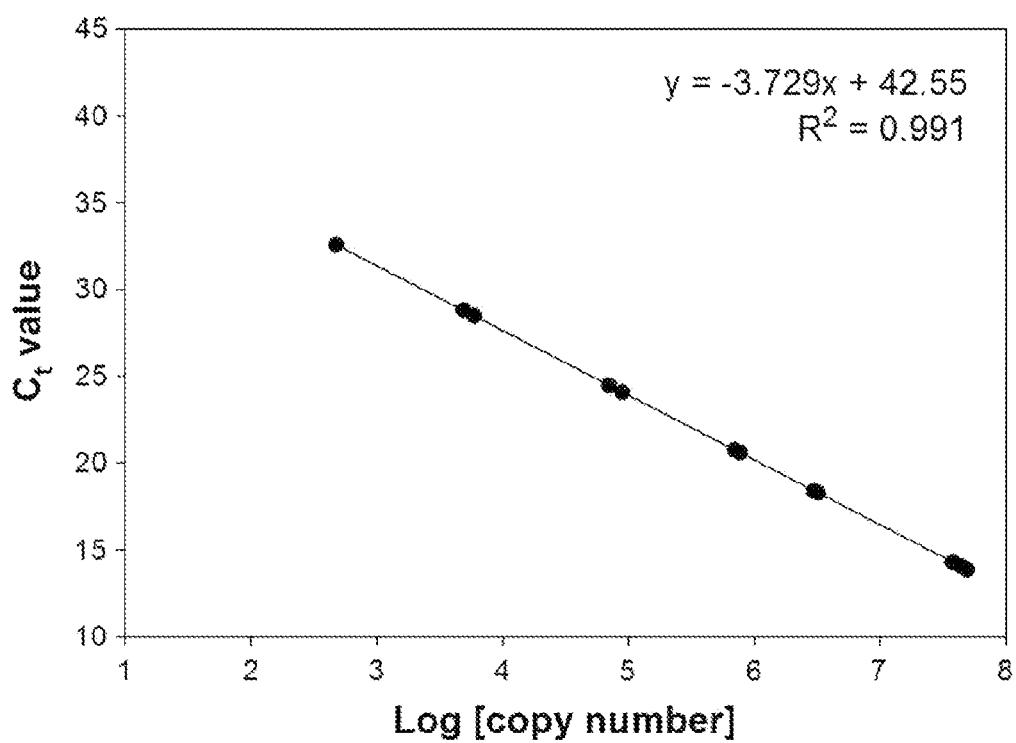
FIGS. 7A and 7B show electrophoresis results after RT-PCR and the results of quantifying norovirus according to an exemplary embodiment of the present invention.
Figure 7B:
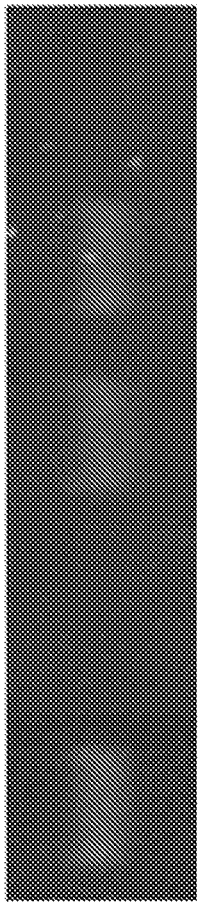

FIG. 7A is the standard curve (y=−3.729x+42.55, and $R^2$=0.991) obtained by the above method. From a y intercept of 42.55, it could be seen that all the values amplified within 42 cycles of real-time RT-PCR were reliable, and from the R value, it could be seen that amplification could be efficiently performed.

Through the equation obtained from the standard sample, it was found that the sample dilution used in the experiment contained about 3.39 copies/μL of norovirus. The virus concentrated through the Con A-linked resin column was quantified to be about 2.16 copies/μL. However, no $C_t$ value was found in the non-Con A-linked resin, but about 2.15 copies/μL of norovirus was detected in the filtrate passed through the column.

Example 4

Comparison of the Efficiency with which Hepatitis A Virus is Detected in Fresh Vegetables The efficiencies of detecting hepatitis A virus concentrated from fresh vegetables in the present invention and a conventional technology were compared.

As the conventional technology, a method of eluting virus with a beef extract-containing eluent and concentrating the eluate by PEG were used. For concentration of virus by Con A, the precipitation method described in Example 3-1) was used. A more detailed experimental method is as follows.

Hepatitis A virus diluted to a concentration of about $10^3$ $TCID_{50}$ was inoculated 10 times into 10 g of lettuce in an amount of 20 μL each time, and the lettuce was dried on a clean bench for 30 minutes, thereby preparing a sample.

40 mL of Tris solution and 40 mL of an aqueous solution containing 5 mg of the crude protein (prepared in Example 1) dissolved therein were added to the sample, and physical shock was applied to the solution using a stomaker (SIBATA Science Technology, Japan) for 5 minutes, followed by stirring for 10 minutes. After 10 minutes, the solution was centrifuged at 15,000×g and 4° C., and the viral supernatant was collected. Acetone stored at −20° C. was added to the supernatant in 6-fold volume of the sample, and the solution was stirred, and then centrifuged at 2,000 rpm for 3 minutes to collect the concentrated protein. A subsequent process was performed in the same manner as described in Example 3-1)-(2), thereby detecting hepatitis A virus.

For comparison, 80 mL of a beef extract-containing eluent (100 mM Tris-HCl, 50 mM glycine, 1% beef extract, pH 9.5) was added to the hepatitis A virus-infected lettuce prepared in the same manner as described above, and physiological shock was applied to the solution using a stomaker (SIBATA Science Technology, Japan) for 5 minutes, followed by stirring for 10 minutes. After 10 minutes, the solution was centrifuged at 15,000×g and 4° C., and the viral supernatant was collected. A two-fold volume of PEG solution containing 16% PEG 6000 (Sigma Chemical Co., St. Louis, Mo., USA) and 0.525 M NaCl was added to the supernatant and allowed to react for 10 minutes. Next, the reaction solution was centrifuged at 2,000 rpm for 3 minutes to collect the concentrated protein, and hepatitis A virus was detected in the same manner as described in Example 3-1)-(2).

FIG. 8 shows the major characteristics and results of the Con A precipitation method and the PEG precipitation method. As can be seen in FIG. 8, the efficiency of detection of virus was about 2 times greater when the method of the present invention employing the crude protein was used, compared to when the concentration method employing PEG solution was used.

As described above, according to the present invention, virus can be concentrated with high efficiency within a short time, because the reaction time required for concentration of virus is only about 5 minutes to 1 hour. In addition, the virus concentration method according to the present invention can be performed using Con A in the form of crude protein, and thus does not require expensive chemicals, expensive equipment or expert technology, suggesting that the virus concentration method of the present invention can concentrate virus in a convenient and cost-effective manner.

In the present invention for virus detection, the virus was concentrated with the binding to the resin in the elution process, and thus a separate reaction time is not required. Accordingly, the virus detection method of the present invention can be effectively used for rapid detection of virus, particularly in food materials.

What is claimed is:

1. A method for concentrating virus, comprising the steps of:
   (A) adding a Concanavalin A to a sample solution containing a virus and reacting the added Concanavalin A with the virus to form a virus—Concanavalin A conjugate; and
   (B) separating the virus-Concanavalin A conjugate from the sample solution, wherein said virus is norovirus or hepatitis A virus.

2. The method of claim 1, wherein the Concanavalin A is a crude protein obtained by a method comprising the steps of:
   (a) extracting ground beans with water to obtain an aqueous extract;
   (b) collecting a pellet fraction, which is precipitated with ammonium sulfate at a saturation degree of about 0.4-0.8, from the aqueous extract; and
   (c) removing ammonium sulfate from the pellet fraction.

3. The method of claim 1, wherein the reacting in step (A) is performed for 5 minutes to 1 hour.

4. The method of claim 1, wherein step (B) comprises adding an acetone to the reaction solution of step (A) to precipitate the virus-Concanavalin A conjugate, and collecting the precipitated virus-Concanavalin A conjugate.

5. The method of claim 1, wherein the Concanavalin A in step (A) is added in a state in which it is linked to a magnetic bead.

6. The method of claim 1, wherein the Concanavalin A in step (A) is added in a state in which it is linked to a resin.

7. A method for detecting virus, comprising steps of:
   (A) preparing a sample solution containing a virus from a sample;
   (B) concentrating the virus in the sample solution by adding a Concanavalin A to the sample solution and reacting the added Concanavalin A with the virus to form a virus—Concanavalin A conjugate, and separating the virus-Concanavalin A conjugate from the sample solution, thereby obtaining a virus concentrate; and
   (C) detecting the virus in the virus concentrate, wherein said virus is norovirus or hepatitis A virus.

8. The method of claim 7, wherein the sample in step (A) is a solid sample, and the sample solution is prepared by eluting the virus from the solid sample.

9. The method of claim 8, wherein a step of eluting the virus is performed simultaneously when the added Concanavalin A reacts with the virus.

10. A water purification method comprising passing water containing a virus through a Concanavalin A-linked resin, wherein said virus is norovirus or hepatitis A virus.

* * * * *